United States Patent [19]

Struthers et al.

[11] Patent Number: 5,702,444
[45] Date of Patent: Dec. 30, 1997

[54] IMPLANTABLE ARTIFICIAL ENDOCRINE PANCREAS

[75] Inventors: Ralph C. Struthers, Saugus, Calif.; Devendra V. Mehta, Bloomfield Hills, Mich.

[73] Assignee: Struthers, Mehta and Maxwell

[21] Appl. No.: 526,075

[22] Filed: Sep. 11, 1995

[51] Int. Cl.$^6$ .................................................. C12N 11/10
[52] U.S. Cl. .............................................. 623/11; 435/178
[58] Field of Search ........................... 623/11; 435/178, 435/268; 210/265, 645

[56] References Cited

U.S. PATENT DOCUMENTS

| | | | |
|---|---|---|---|
| 4,323,457 | 4/1982 | Sun | 210/645 |
| 4,391,909 | 7/1983 | Lim | 435/178 |
| 5,079,160 | 1/1992 | Lacy | 435/268 |
| 5,160,313 | 11/1992 | Carpenter | 623/901 |
| 5,262,055 | 11/1993 | Bae | 210/265 |
| 5,322,790 | 6/1994 | Scharp | 435/268 |
| 5,344,454 | 9/1994 | Clarke | 623/11 |
| 5,545,223 | 8/1996 | Neuenfeldt | 623/11 |
| 5,549,675 | 8/1996 | Neuenfeldt | 623/11 |

*Primary Examiner*—Michael J. Milano
*Attorney, Agent, or Firm*—Georges A. Maxwell

[57] ABSTRACT

An implantable artificial endocrine pancreas comprising a reactive body of soft, plastic, biocompatible, porous hydratable material supporting a multiplicity of endocrine pancreatic islets in isolated spaced relationship from each other; and, a microporous barrier membrane enveloping and supporting the body, in spaced relationship from the pancreatic islets therein and through which molecules having a molecular weight greater than 60,000 Daltons cannot move.

10 Claims, 3 Drawing Sheets

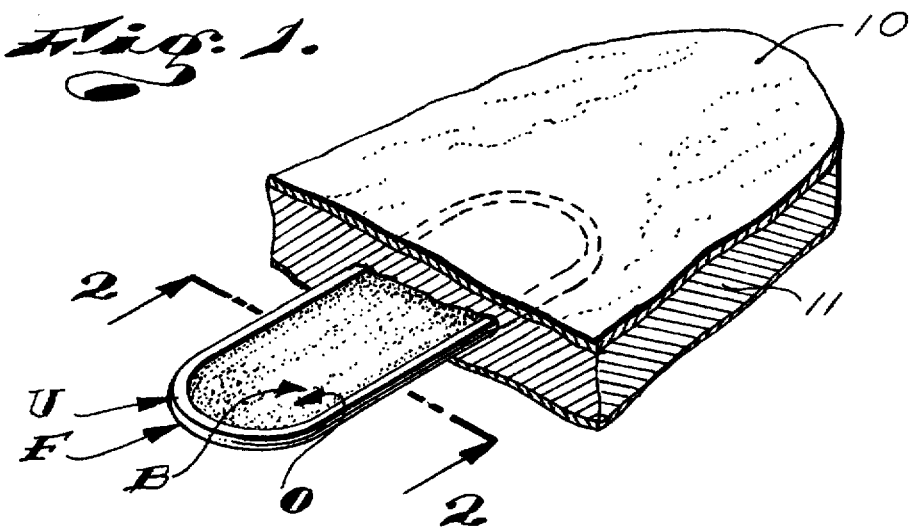
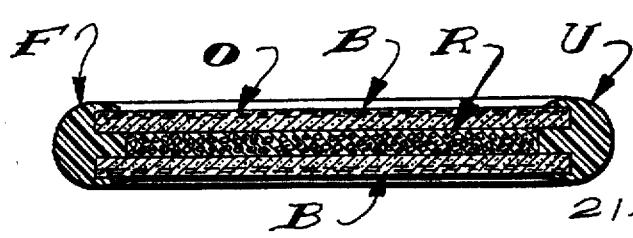
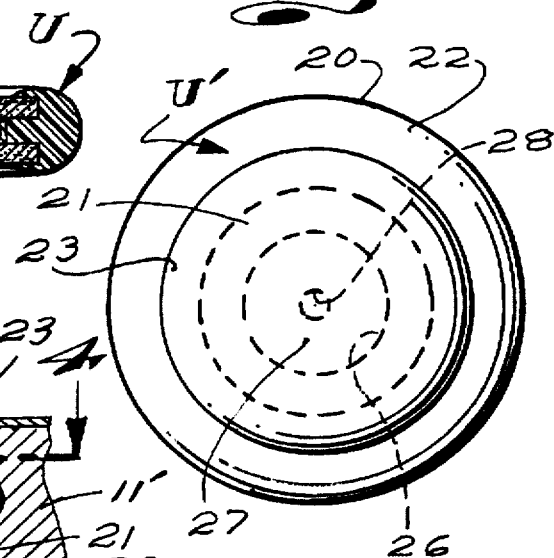
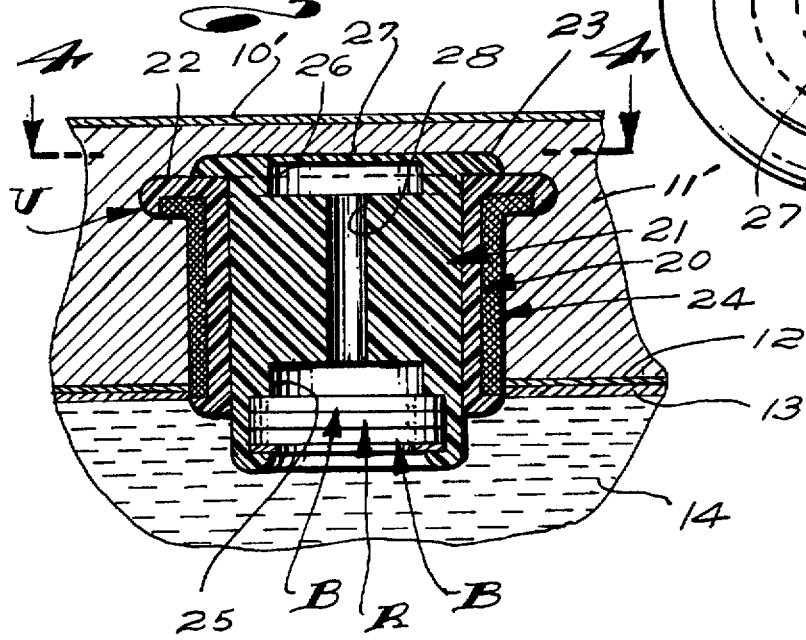

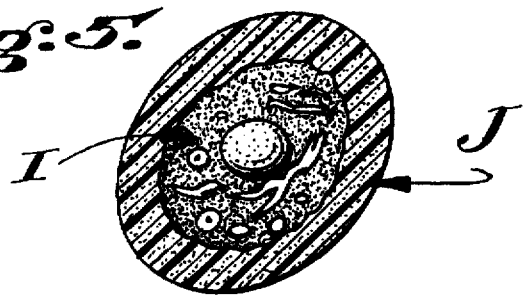
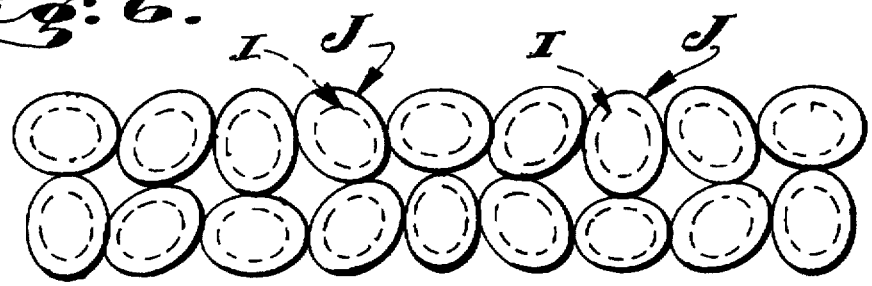
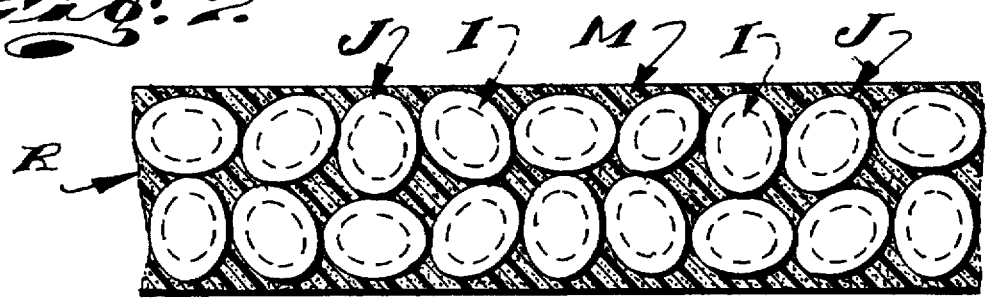
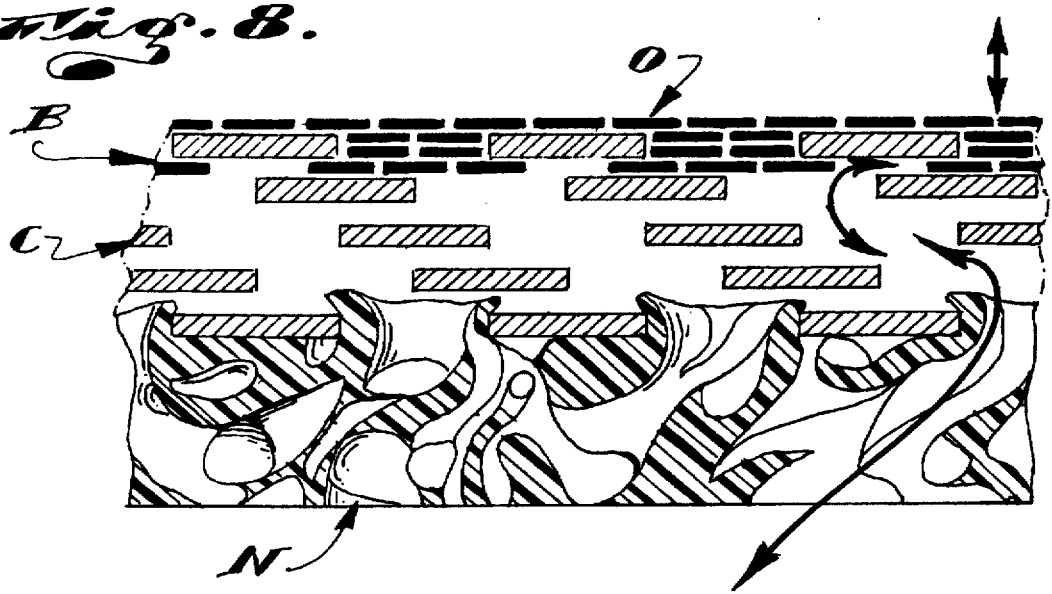

Fig. 9.

TABLE 1

| ******ISLET CELL DATA**** | | | VOLUME OF REACTOR SYSTEM | | | | ONE CELL | TOTAL CELLS | TOTAL CELLS** |
|---|---|---|---|---|---|---|---|---|---|
| DIAMETER | CELL VOL. | ISLET CELLS | ISLETS | PHASIC | SPACE | TOTAL | U INSULIN / HR. | U INSULIN / HR. | IU INSULIN / HR. |
| Microns | ML | Total Count | ML | ML | ML | ML | 300mg/dL Glucose | 300mg/dL Glucose | 50mg/dL Glucose |
| 350 | 0.0000224 | 73,054 | 1.64 | 2.06 | 0.41 | 4.11 | 0.0007072 | 51.7 | 0.6 |
| 198 | 0.0000041 | 403,500 | 1.64 | 2.54 | 0.51 | 4.69 | 0.0001280 | 51.7 | 0.6 |
| 75 | 0.0000002 | 7,424,384 | 1.64 | 4.73 | 0.95 | 7.31 | 0.0000070 | 51.7 | 0.6 |

NOTE: 20 MICRONS SPACING BETWEEN ADJACENT ISLET CELLS.

| ******ISLET CELL DATA**** | | | VOLUME OF REACTOR SYSTEM | | | | ONE CELL | TOTAL CELLS | TOTAL CELLS** |
|---|---|---|---|---|---|---|---|---|---|
| DIAMETER | CELL VOL. | ISLET CELLS | ISLETS | PHASIC | SPACE | TOTAL | U INSULIN / HR. | U INSULIN / HR. | IU INSULIN / HR. |
| Microns | ML | Total Count | ML | ML | ML | ML | 300mg/dL Glucose | 300mg/dL Glucose | 50mg/dL Glucose |
| 350 | 0.0000224 | 73,054 | 1.64 | 2.69 | 1.08 | 5.41 | 0.0007072 | 51.7 | 0.6 |
| 198 | 0.0000041 | 403,500 | 1.64 | 3.80 | 1.52 | 6.96 | 0.0001280 | 51.7 | 0.6 |
| 75 | 0.0000002 | 7,424,384 | 1.64 | 9.65 | 3.86 | 15.2 | 0.0000070 | 51.7 | 0.6 |

NOTE: 40 MICRONS SPACING BETWEEN ADJACENT ISLET CELLS.

| ******ISLET CELL DATA**** | | | VOLUME OF REACTOR SYSTEM | | | | ONE CELL | TOTAL CELLS | TOTAL CELLS** |
|---|---|---|---|---|---|---|---|---|---|
| DIAMETER | CELL VOL. | ISLET CELLS | ISLETS | PHASIC | SPACE | TOTAL | U INSULIN / HR. | U INSULIN / HR. | IU INSULIN / HR. |
| Microns | ML | Total Count | ML | ML | ML | ML | 300mg/dL Glucose | 300mg/dL Glucose | 50mg/dL Glucose |
| 350 | 0.0000224 | 73,054 | 1.64 | 3.39 | 2.04 | 7.07 | 0.0007072 | 51.7 | 0.6 |
| 198 | 0.0000041 | 403,500 | 1.64 | 5.29 | 3.17 | 10.1 | 0.0001280 | 51.7 | 0.6 |
| 75 | 0.0000002 | 7,424,384 | 1.64 | 16.6 | 9.98 | 28.2 | 0.0000070 | 51.7 | 0.6 |

NOTE: 60 MICRONS SPACING BETWEEN ADJACENT ISLET CELLS.

| ******ISLET CELL DATA**** | | | VOLUME OF REACTOR SYSTEM | | | | ONE CELL | TOTAL CELLS | TOTAL CELLS** |
|---|---|---|---|---|---|---|---|---|---|
| DIAMETER | CELL VOL. | ISLET CELLS | ISLETS | PHASIC | SPACE | TOTAL | U INSULIN / HR. | U INSULIN / HR. | IU INSULIN / HR. |
| Microns | ML | Total Count | ML | ML | ML | ML | 300mg/dL Glucose | 300mg/dL Glucose | 50mg/dL Glucose |
| 350 | 0.0000224 | 73,054 | 1.64 | 4.17 | 3.33 | 9.14 | 0.0007072 | 51.7 | 0.6 |
| 198 | 0.0000041 | 403,500 | 1.64 | 7.03 | 5.62 | 14.3 | 0.0001280 | 51.7 | 0.6 |
| 75 | 0.0000002 | 7,424,384 | 1.64 | 26.0 | 20.8 | 48.5 | 0.0000070 | 51.7 | 0.6 |

NOTE: 80 MICRONS SPACING BETWEEN ADJACENT ISLET CELLS.

IMPLANTABLE ARTIFICIAL ENDOCRINE PANCREAS

BACKGROUND OF THE INVENTION

Due to various causes, including disease, poisoning and injury, the insulin-producing pancreas glands of many persons fail to produce insulin or fail to produce sufficient insulin to sustain life. Those persons are called diabetics.

For many years, insulin has been extracted from donor pancreases and administered to diabetics in order to sustain their lives.

In recent years, the prior art has determined that endocrine pancreatic, islets harvested from the pancreas of humans and certain animals, such as pigs, when implanted in diabetic patients produce insulin sufficient to meet the patient's needs, when and as the patient's system demands.

As a result of the foregoing, there has been a long and continuing search to discover and develop effective means for implanting harvested endocrine pancreatic islets in the bodies of diabetics. Prior to our invention, those means for implanting pancreatic islets in diabetics have proven to be wanting in one or more respects.

One noticeable problem encountered when pancreatic islets from foreign sources are implanted in diabetics resides in the fact that the T-cells of the diabetics' immune systems attack and destroy the pancreatic islets. Efforts by the prior art to protect implanted islets from attack by T-cells and the like have resulted in many different protector means but none of those means has proven to be wholly satisfactory and to meet general acceptance in the medical arts.

Another noticeable problem encountered by the prior art upon implanting harvested endocrine pancreatic islets resides in the rapid dying off of excess numbers of implanted pancreatic islets and poor functioning of many of the islets that survive. The foregoing is brought about by the fact that islets, to live and function properly when implanted, must be supported freely so that the body fluids of the patient that carry nutrients and hormones to the islets and that carry away the insulin and other products of the islets, flow about and surround the whole of the islets in sufficient volume so that functioning of the islets is in no way impeded.

To the best of our knowledge and belief, prior to our invention, the art has failed to provide an effective way or means to support and carry a multiplicity of islets, for implanting, in effective spaced relationship, one from the other. Some in the prior art have resorted to increasing the number of islets in clusters of interengaging islets in an effort to compensate for anticipated dying off of islets. Others have sought to arrange multiplicities of adjacent or abutting islets in elongated or flattened clusters in an effort to increase the number of islets that are sufficiently exposed to survive and function.

In each of the above-noted cases, only those pancreatic islets that occur at the exterior surface of the clusters of islets are unmasked and/or exposed and free to receive nutrients from and deliver insulin to body fluids that are in contact therewith.

Further, the capacity of those islets occurring at the surface of clusters of islets to produce insulin is limited proportionately to that portion of the surface area of the islets that are adequately exposed to the patient's body fluids. Those islets which occur within the clustered islets receive no or inadequate nutrients to sustain life and soon die.

PRIOR ART

The process of isolating islet cells is described in U.S. Pat. No. 5,322,790, issued to David W. Scharp and Paul E. Lacy on Jun. 21, 1994 and entitled, "ISLET ISOLATION PROCESS."

The manufacture of artificial pancreas described in U.S. Pat. No. 5,262,055, issued to You H. Nae and Sun W. Kim on Nov. 16, 1993 and entitled, "IMPLANTABLE AND REFILLABLE BIOHYBRID ARTIFICIAL PANCREAS."

The process of preparing islet cells for transplantation is described in U.S. Pat. No. 5,160,313, issued to John F. Carpenter and Kelvin G. M. Brockbank on Nov. 3, 1992 and entitled, "PROCESS FOR PREPARING TISSUE FOR TRANSPLANTATION."

The process of isolating islet cells is described in U.S. Pat. No. 5,079,160, issued to Paul E. Lacy, David W. Scharp and Camillo Ricordi on Jan. 7, 1992 and entitled, "METHOD TO ISOLATE CLUSTERS OF CELL SUBTYPES FROM ORGANS."

The manufacture of an artificial pancreas described in U.S. Pat. No. 4,391,909, issued to Franklin Lim on Jul. 5, 1983 and entitled, "MICROCAPSULES CONTAINING VIABLE TISSUE CELLS."

The manufacture of artificial pancreas described in U.S. Pat. No. 4,323,457, issued to Anthony M. Sun and Wolf J. Parisius on Apr. 6, 1982 and entitled, "ARTIFICIAL ENDOCRINE PANCREAS."

OBJECTS AND FEATURES OF THE INVENTION

It is an object of our invention to provide a novel, artificial, implantable endocrine pancreas structure including endocrine pancreatic islets and that is particularly suited for implantation in diabetic patients.

Another object of our invention is to provide a novel implantation structure for the purpose set forth above that conserves of the number of pancreatic islets that must be used and better assures both the effective functioning and useful life of those islets that are used.

Yet another object of our invention is to provide an implantable artificial endocrine pancreas structure of the general character referred to above wherein the islets are effectively protected against attack and/or destruction by T-cells of a patient's immune system and other molecules and matter that might kill or adversely affect functioning of the islets.

It is object and feature of our invention to provide an endocrine implant structure of the general character referred to above wherein a multiplicity of pancreatic islets are supported and held in isolated spaced relationship from each other within a mass or body of soft, plastic, biocompatible porous material through which ample volumes of body fluid are free to flow to and about the islets to supply nutrients and hormones to the whole of the exterior surface of each islet and to receive and carry from each islet the insulin and other products thereof.

A further object and feature of our invention is to provide an implant structure of the general character referred to above wherein the pancreatic islets are positioned in isolated and spaced relationship from each other by protective spacer jackets of biocompatible, soft, plastic, porous material through which body fluids are free to flow to supply nutrients and hormones to the islets and to receive and carry from the islets the products thereof; and, a structure wherein the abutting jackets of adjacent islets maintain those islets in noninterferring spaced relationship from each other within the structure for the free flow of nutrient and hormone carrying body fluids thereabout.

Finally, it is an object of our invention to provide an implant structure of the general character referred to above that is easy and economical to produce, that can be stored and made ready for use for protracted periods of time; and, that is such that it can be easily and conveniently made in different sizes and configurations to facilitate its being related to various means and/or structures that might be utilized to effect implantation thereof.

The foregoing and other objects and features of our invention will be apparent and will be fully understood from the following detailed description of typical preferred forms and embodiments of our invention throughout which description reference is made to the accompanying drawings.

DESCRIPTION OF THE DRAWINGS

FIG. 1 is a isometric view of one preferred form of implant device embodying our invention and showing it implanted in a portion of a patient's body;

FIG. 2 is a sectional view taken substantially as indicated by Line 2—2 on FIG. 1;

FIG. 3 is a sectional view of another implant device embodying our invention and showing it implanted in a portion of a patient's body;

FIG. 4 is a view taken substantially as indicated by Line 4—4 on FIG. 3;

FIG. 5 is a sectional view depicting a single endocrine pancreatic islet with a protector-spacer jacket about it;

FIG. 6 is a view showing a plurality of jacketed pancreatic islets in adjacent relationship with each other;

FIG. 7 is a view similar to FIG. 6 with a matrix material added to establish a unitized reactor body;

FIG. 8 is a diagrammatic view depicting the structural nature of the barrier membrane of our invention; and, FIG. 9 is a table setting forth data pertaining to certain physical characteristics of the invention.

DETAILED DESCRIPTION OF THE INVENTION

The present invention has to do with an artificial endocrine pancreas structure or device P for implantation in diabetic patients. The device P is a poly-sac device that includes an inner or central active reactor body R of biocompatible, porous, hydratable material in which a multiplicity of endocrine pancreatic islets I (harvested from donor pancreas) are supported in spaced relationship from each other; and, a barrier membrane B at and about the exterior surfaces of the reactor body R to support that body and that creates a barrier through which T-cells of a patient's immune system and other deleterious matter carried by the body fluids of the patient cannot pass and enter the reactor body R and attack the islets I therein, while allowing for the free movement of body fluids therethrough to supply the islets I within the body R with necessary nutrients and hormones for the production of insulin and other products of the islets; and, to receive and carry the insulin and other products of the islets from the device into the body of the patient.

It is highly important to note that the ability of endocrine pancreatic islets to live and function efficiently and effectively is dependent upon their exterior surfaces being free of masking and such that the body fluids that sustain their lives and control their functioning to produce insulin, glucagon and other of their products is substantially free to move into and out of contact with the whole of their exterior surfaces.

If not suitably managed and controlled, pluralities of harvested pancreatic islets tend to cluster together. When islets are clustered together, those islets within the cluster are starved of nutrients, fail to function and soon die. Those islets about the exterior surfaces of clusters of islets and that continue to receive sufficient nutrients will continue to live and function but their vigor and capacity to produce insulin and other of their products is reduced to a degree that is substantially proportionate to the portion of their surface area that is not masked and deprived of sufficient body fluids to live and function vigorously.

To the best of our knowledge and belief, those in the prior art who have sought to harvest foreign pancreatic islets and implant them in diabetic patients have failed to utilize effective and efficient means to maintain the islets spaced apart. Instead they have allowed the islets to cluster or otherwise come into contact with each other. As a result of the foregoing, following implantation of islets that are clustered-together, those islets within the clusters of islets and that are masked from adequate supplies of body fluid, soon die. The islets at the surfaces of the clusters of islets, a portion of the surfaces of which are exposed to adequate supplies of body fluid, do not live vigorously and function poorly.

In furtherance of our invention, as shown in FIG. 5 of the drawings, each of the harvested or foreign islets I that we use to establish our new reactor body R is first coated with a suitable biocompatible, microporous hydrogel or similar material that is sufficiently structurally stable, when set, to create a porous jacket J about the islet to serve to protect the islet and to maintain it spaced from adjacent structures, including adjacent islets. The thickness of the jacket J can be varied as desired and as circumstances require. In practice, the thickness of the jacket J is at least equal to one-half the minimum distance that is sought to be maintained between adjacent islets and such that the contacting jackets of adjacent pairs of islets maintains those islets spaced, as desired.

With the above combination and relationship of parts, only that number of jacketed islets that are required to be used need be used; the islets that are used are most effectively spaced apart from each other to assure vigorous life and maximum functioning; and, the volumetric space required to accommodate the multiplicity of islets used can be more easily and accurately determined and maintained at a minimum.

In practice, the jacketed islets might be stored and used in loose form. However, to facilitate handling and use of the jacketed islets and to afford them with necessary support, we have found it highly advantageous that they be spread uniformly over the top of a suitable flat surface together with a suitable biocompatible, microporous matrix material that when set or cured creates a support body or a matrix M that serves to support and maintain the jackets J (with the islets therein) in desired form and desired spacial relationship. The jacketed islets within the matrix create a thin flat sheet of islet-laded active reactor body stock from which reactor bodies R of desired configuration and size can be cut for present use or for storage and subsequent use.

In practice, the prepared reactor bodies R can be air dried (partially dehydrated), suitably wrapped and stored at a suitable low temperature until it is desired to put them to use. The storage life of the islets when stored, as noted above, is in excess of nine months. When refrigerator-stored bodies R are put to use, they are let to warm to ambient temperature and are rehydrated with a saline solution that permeates the matrix M, jackets J, and the islets I and awakens the islets from their earlier dormant or hibernating state.

In practice, polyvinyl alcohol and sodium alginate can be used to establish the matrix and to bind the jacketed islets together. As the material of the matrix M cures or/sets it welds with the surfaces of the jackets J to establish a single body of material within which the islets are supported in spaced relationship from each other.

In practice, the material of which the support body or matrix M is made is preferably a more stable and stronger material than the material of which the jackets J are made. The matrix material preferably is a thin porous material that is applied onto and between the assembly of jacketed islets and that creates a net-like or reticulate structure, when cured, that supports the jacketed islets against deformation and in set spaced relationship from each other.

It is to be noted that the materials utilized to establish the jackets J and the matrix M are sufficiently soft, flexible, resilient and plastic to provide cushioned support and protection for the islets and work to maintain intimate supporting contact with and about the surfaces of the islets at all times (should the islets grow or shrink in size) and to thereby assure free movement of materials into and from the islets throughout the whole of the exterior surfaces thereof.

In Table I presented in FIG. 9 of the drawings, data for our reactor bodies with islets ranging in size from 198 to 350 microns are set forth. As a general rule, the larger an islet is and the more effective surface area it presents, the more insulin it produces. Accordingly, as the size of islets increases, the number of islets to produce a required amount of insulin is reduced. Further, as the size of islets increases, the spacing between adjacent islets might be increased to attain and maintain most effective functioning of the islets.

The required amount of insulin from islets for an adult male is about 52 units per hour at 300 mg/dL of glucose. A healthy, well functioning islet of average size, which is about 198 microns, can produce about 0.0001280 units of insulin per hour at 300 mg/dL of glucose. Accordingly, our new reactor body R must contain and carry no less than 403,500 islets to serve the needs of an average adult male. When practicing our invention, the establishing of a reactor body R including a minimum number of islets plus a limited and predeterminable number of extra or spare islets can be easily and economically produced.

As regards the spacing apart of islets, as noted in Table I, there is a readily determinable minimum distance that must be maintained between adjacent islets if the islets are to sustain vigorous life and function well. That minimum distance is less than the diametric extent of the islets. Accordingly, the space requirement for a suitable and predetermined number of islets, in our invention, is notably less than the space that is required to accommodate clusters of interengaged islets that are of sufficient size to present, at the surfaces of the clusters, a sufficient number of islets, exposed to body fluids, to produce that insulin that might be needed.

Referring to FIG. 8 of the drawings, the barrier membrane B is a laminated structure that includes a porous central carrier layer C that has inside and outside surfaces; a microporous exterior or outside layer O at the exterior or outside surface of the carrier C; and, a porous interior or inside layer N at the inside surface of the carrier layer C.

The carrier layer C is preferably established of a suitable polymer such as polysulfone, preferably having a pore size less than 0.1 micron.

The exterior layer O of the barrier membrane B is a molecular cut-off layer that is deposited on and anchored to the outer surface of the carrier C and that has a pore size capable of excluding the passage of all materials having a molecular weight of 60,000 Daltons (such as T-cells of the human immune system) or greater; while allowing for the free passage there through of matter or material, such as body fluids and the nutrients and hormones carried thereby. Such matter or materials includes those hormones that stimulate and/or trigger functioning of the islets and the products of the islets, such as insulin, the molecular weight of which is near 5,033.

The primary function of the outer layer O of the barrier membrane B is to prevent T-cells, bacteria and other destructive molecular species from moving through the membrane B, matrix M and jacket J where they would otherwise attack and kill or otherwise cause irreparable harm to the islets I.

In practice, certain polymers of cellulose derivatives are quite suitable for deposition on the outer surface of the carrier layer C to establish the outer cut-off layer O.

The inner layer N of the barrier membrane B, the matrix M and the jackets J about the islets I can be established of materials selected from a considerable number of different materials that lend themselves for use in our invention.

The material of the layer N is deposited on and anchored to the inside surface of the carrier layer C and is provided to establish a soft, flexible, cushion-like barrier between the carrier layer C and the matrix M and those jacketed islets I that might occur at the surface of the matrix M and are engaged by the membrane B.

It will be apparent that in practice, the inside layer N of the barrier membrane B can be eliminated. In such a case, care must be taken so that the jacketed islets are spaced inward from the surface of the matrix that opposes the membrane. For example, the material to establish the layer N on the inside surface of the membrane B might be applied to the surface of the matrix M that opposes the membrane B without departing from the broader aspects and spirit of our invention. Alternatively, the matrix M of the body R might be a lattice structure that is made or built up to overlie and protect those jacketed islets that would otherwise occur at the surfaces of the body R.

The barrier membrane B occurs about and overlies the exterior surfaces of the reactor body R with the inside surfaces of the membrane in intimate contact and supporting engagement with the exterior surfaces of the matrix M of the body R.

In practice, for example, the outer layer O of the membrane B can be approximately 0.010" thick. The carrier C of the membrane can be approximately 0.010" thick; and, the inside layer N can be approximately 0.060" thick. In such a case, the total thickness of the membrane B is approximately 0.080" thick.

The material of which the membrane B is made is preferably established in large sheets from which membrane parts can be cut, as desired and as circumstances require.

In FIGS. 1 and 2 of the drawings, we have illustrated an implant device or unit U embodying our invention. The device or unit U is shown surgically implanted in a diabetic patient beneath the epidermis 10 and within the subcutaneous fat 11 where all of its exterior surfaces are contacted by the patient's subcutaneous body fluids.

The device U is shown as a small flat horizontally disposed unit with upwardly and downwardly disposed top and bottom surfaces that are defined by the outer cut-off layers O of upper and lower barrier membrane parts B. Between the membrane parts B is our islet-carrying reactor body R. About the perimeter of the assembled body R and membrane parts B is a frame F established of a biocompatible plastic material that is suitably secured or fixed with and between the perimeter edges of the parts B, to sealingly fix the edges of the parts B together, with the body R therebetween.

The plan configuration of the unit U and the exterior surfaces of the frame F are radiused and/or parabolically curved to eliminate the presentation of sharp exterior corners, edges and the like that might otherwise cause adverse effects within the patient's body.

In FIGS. 3 and 4 of the drawings, we have illustrated another form of implant unit or device U' embodying our invention. The device U' is shown surgically planted beneath the epidermis 10' of a diabetic patient and extending through the subcutaneous fat 11', fascia 12 and peritoneal membrane 13 into the peritoneal body fluid 14, within the patient's body.

The unit U' includes an elongate, tubular, vertically extending receptacle 20 that is preferably made of a suitable biocompatible plastic material and an elongate cylindrical bobbin 21 that is made of a similar material. The bobbin is axially slidably moveable into and out of engagement in the receptacle 20, at the upper end thereof.

The receptacle 20 is formed with a horizontally disposed radially outwardly projecting seat flange 22 at its upper end. The bobbin 21 is formed with an outwardly projecting stop flange 23 that normally engages the top of the flange 22 to limit downward movement of the bobbin within the receptacle.

The flanges 22 and 23 occur in close proximity to the underside of the epidermis 10'. The lower end of the bobbin normally projects downwardly from within the receptacle, a limited distance.

Ve Lour graft material 24 is bonded to the exterior surfaces of the receptacle to promote ingrowth of the patient's tissue to anchor the receptacle 20 in place within the patient's body.

The lower end of the bobbin is formed with a downwardly opening cavity 25 in which a preestablished artificial endocrine pancreas body R embodying our invention is positioned, as shown. The lower barrier membrane B of the body R is substantially fully exposed to and is contacted by the patient's peritoneal fluids.

It will be apparent that the bobbin 21 can be gained access to, for removal and replacement of the bobbin, by a simple surgical operation, under local antiseptic and/or anesthetic.

In addition to the foregoing, the bobbin 21 can, as shown, be formed with a small chamber 26 in its upper end. The upper end of the chamber 26 is closed by a needle septum 27. A fluid passage 28 extends between the chamber 26 and the cavity 25.

With the above-noted structure, it is possible to feed the body R with nutrients or introduce antibiotics or the like into the unit. It is also possible to extract islets from or inject new islets into the body R, by means of a hypodermic syringe, if circumstances require.

The two devices or units U and U' shown in the drawings and briefly described above are illustrative of but two typical forms of implantation devices or units that embody our invention. It will be apparent that in practice various other structures might be advantageously used to effect putting our invention to its intended use.

Set forth in the following are examples of particular materials and processes that have been advantageously used to establish the jackets J and the matrix M of the active reactor body R of our invention. Reference is to be made to the data included in the Table I of FIG. 9 of the drawings in which; the micron diameters of several different sizes of islets that might be used is set forth; the required number of islets; the required micron spacing between adjacent islets; the required milliliters of stabilized islets of Langerhans pig islets; and, the required milliliters of hydrogel gum solution required to establish an active islet reactor unit R embodying each size of islet is set forth.

The jackets about the islets are established as follows. A dilute hydrogel gum solution is prepared from equal amounts by volume of dilute solution of 8.0 percent sodium alginate solution in physiologically saline to which is added an 8.0 percent solution of polyethyleneamine (Mol. Wt. 40,000–60,000) cross-linking agent in a 0.2M (pH=6.0) buffer of morpholino propane sulfonic acid. To the above hydrogel solution is added, drop-wise, stabilized islets of Langerhans pig islets I, or xenografts from foreign species, at a desired concentration of cells per volume of jacket-forming material. Stirring of these materials is continued for about 30 minutes to obtain a uniform jacket J about each islet cell I. Thereafter, to establish the matrix M and while stirring of the jacketed islets continues, we add, drop-wise, a 12.0 percent weight/volume solution of polyvinyl alcohol (PVA) to form the matrix M around and between the jacketed islet cells. This mixture is stirred for about 30 minutes and is then cast on a flat casting surface (glass plate) to establish a sheet of required thickness and carrying a predetermined number of islets per area unit. The cast sheet is then air-dried to form islet reactor body stock in film or sheet form. The sheet stock is then cut to establish reactor bodies R of required size and form. The reactor bodies R, thus formed, can be put to immediate use or can be cold stored.

It will be apparent to those skilled in the art of making films, coatings, encapsulations and membrane fabrication, that the islet reactor body R that we provide might be formed directly on an appropriate surface of the barrier membrane B without departing from the broader aspects and spirit of our invention.

The jackets J about the islets I are preferably made of a hydrogel gum that is devoid of cross-linking and that is quite soft and plastic. The hydrogel formulation can consist of, but is not limited to, any one of numerous suitable gum alginates, guar gums, agars, agaroses and carrageens.

The matrix M can be made of a suitable compatible water-soluble polymer such as, though not limited to, hydroxy celluloses, polyvinyl alcohols, polyvinyl pyrrolidones, etc. The material of which the matrix is made is cross-linked and suitably dimensionally stable to effectively hold and maintain the jacketed islets in set position.

Preparation of outer cut-off barrier O of barrier membrane B is made as follows:

A dilute solution of 7 to 11 weight/volume percent cellulose acetate (39.9 acetyl content) in glacial acetic acid is used for spin coating the membrane support of 0.1 micron polysulfone, PS, carrier C, mounted on a vacuum-suction table of a spin coater and allowed to rotate at 10,000 to 15,000 rpm. The dilute cellulose acetate solution dispensed on the rotating PS membrane surface and the operation repeated three times. The coated surface allowed to vacuum dry, followed by placement in 0.1N NaOH for 24 hours, to regenerate the cellulose via hydrolysis. The dry cut-off barrier O has molecular weight cut off of about 60,000 Daltons.

The cut-off barrier O can be made of cellulosic derivatives, though not limited to can include regenerated cellulose and cellulose acetates, cellulose esters or ethers or acrylates, etc.

Preparation of inner layer N of barrier membrane B is made as follows:

A hydrogel gum solution is prepared from equal amounts by volume of a solution of 3.0 percent sodium alginate solution in physiological saline, and a 0.4 percent solution of polyethyleneamine (Mol. Wt. 40,000–60,000) cross-linking agent in a 0.2M (pH=6.0) buffer, morpholino propane sulfonic acid. The mixture is spin coated on the 0.1 micron polysulfone, PS, carrier C, mounted on a vacuum-suction table of a spin coater and allowed to rotate at 10,000 to 15,000 rpm, at s casting thickness of 0.030 inches, air dried to form the protective, rehydratable gel cushion N on the underside, offering the protective barrier and cushioning support to the islet reactor body R.

Preparation of implantable assemblies of our reactor bodies and barrier membranes is as follows:

A reactor body R of desired size configuration is positioned between a pair of barrier membranes B with the surfaces of the matrix M of the body R in supported engagement with the inner surfaces of the layers N of the membranes B. Thereafter, the peripheral portions of the assembly or pack are suitably sealed so that the perimeter edges and/or portions of the body(s) R are sealed to prevent the invasion of those matters and materials that the cut-off layer O of the barrier membranes are designed to exclude. In practice, the perimeters of the packs can be sealed by means of a silastic gasket or frame structure, such as is shown in FIGS. 1 and 2 of the drawings. In other instances, the edge portions of the barrier membranes can be made to project outwardly from the perimeters of the bodies R and can be formed and bonded together with suitable impervious bonding materials or the like. In yet other instances, the exterior or perimeter surfaces of the packs might be painted or coated with a suitable impervious sealant.

In those instances where the bodies R or components thereof have been substantially dehydrated and stored, the packs are rehydrated with an appropriate physiological saline solution prior to implantation.

It is to be noted that the viability of the islets I is greatly dependent upon their being protected and treated with particular care. It has been determined that the material of which the jackets J are formed is preferably a soft and plastic material free of cross-links and such that it affords yielding cushioned support for the islets. Such jackets must themselves be supported and protected against externally applied forces that might cause them to flow and deform about the islets so as to adversely affect their ability to support and maintain the islets of the bodies R in desired spaced-apart relationship. In addition to the foregoing, if the jacketed islets are let to move about and migrate into increasing pressure engagement with each other or into engagement with other structures, the forces applied to the jackets at points of contact tend to compact the soft and porous jacket material and adversely affect the ability of the jackets to conduct those materials that must flow to and from the islets. Accordingly, the provision and inclusion of the matrix M, which is established of a soft, plastic, porous, cross-linked material that serves to support the jacketed islets and prevent their movement and displacement within the bodies R is an important feature of our invention.

Having described only typical preferred forms and applications of our invention, we do not wish to be limited to the specific details herein set forth but wish to reserve to ourselves any modifications and/or variations that might appear to those skilled in the art and that fall within the scope of the following claims.

Having described our invention, we claim:

1. An implantable artificial endocrine pancreas device including a multiplicity of endocrine islets, a jacket of biocompatible, soft, plastic, hydratable porous material about each islet, the jackets about adjacent islets are in bridging contact with each other and support the islets in predetermined spaced relationship with each other, a matrix body of biocompatible, plastic, porous, hydratable material is formed about and between the jacketed islets and supports the jacketed islets in fixed position, a biocompatible barrier membrane structure is positioned in supporting engagement with exterior surfaces of the matrix and includes microporous material that excludes free diffusion and movement of materials the molecular size of which, is greater than 60,000 Daltons.

2. The device set forth in claim 1 wherein the material of which the jackets are made is a hydrogel free of cross-links.

3. The device set forth in claim 1 wherein the material of which the matrix is made is a cross-link hydrogel.

4. The device set forth in claim 1 wherein the materials of which the jackets and matrix are made are hydrogels.

5. The device set forth in claim 4 wherein the hydrogel of which the jackets are made is free of cross-links.

6. The device set forth in claim 4 wherein the hydrogel of which the jackets are made is free of cross-links; and, the material of which the matrix is made is cross-linked.

7. The device set forth in claim 1 wherein the barrier membrane structure is a laminated structure including a carrier layer of substantially dimensionally stable, flexible and porous material with an inside surface opposing the matrix and an oppositely disposed outer surface; and, a layer of microporous material overlying the outer surface of the carrier layer.

8. A biocompatible artificial pancreas device including an exterior barrier membrane structure that excludes free diffusion and movement of material therethrough the molecular size of which is greater than 60,000 Daltons; a matrix of porous plastic hydratable material contained within the barrier membrane structure; a multiplicity of endocrine islets within and carried by the matrix in predetermined minimum spaced relationship one from the other; and, wherein the endocrine islets are encapsulated within jackets of biocompatible, plastic porous material, the wall thickness of the jacket about each islet is equal to at least one-half the predetermined minimum space between adjacent islets.

9. The device set forth in claim 8 wherein jackets about adjacent islets are in contact with each other and supported against deformation and in set position by the matrix.

10. The device set forth in claim 9 wherein the material of which the jackets are made is a non-linked dehydratable and rehydratable hydrogels and the material of which the matrix is made is a cross-linked dehydratable and rehydratable hydrogel.

* * * * *